United States Patent
Wang

(10) Patent No.: US 10,541,061 B2
(45) Date of Patent: Jan. 21, 2020

(54) SYSTEM FOR GENERATING AND COLLIMATING AN X-RAY BEAM

(71) Applicant: KONINKLIJKE PHILIPS N.V., Eindhoven (NL)

(72) Inventor: Chin Wang, Suzhou (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 97 days.

(21) Appl. No.: 15/736,681

(22) PCT Filed: Jun. 22, 2016

(86) PCT No.: PCT/EP2016/064381
§ 371 (c)(1),
(2) Date: Dec. 14, 2017

(87) PCT Pub. No.: WO2017/001256
PCT Pub. Date: Jan. 5, 2017

(65) Prior Publication Data
US 2018/0158562 A1    Jun. 7, 2018

(30) Foreign Application Priority Data

Jun. 29, 2015  (WO) ............... PCT/CN2015/082704
Sep. 29, 2015  (EP) .................................... 15187275

(51) Int. Cl.
*G21K 1/02*      (2006.01)
*A61B 6/06*      (2006.01)
(Continued)

(52) U.S. Cl.
CPC ............... *G21K 1/02* (2013.01); *A61B 6/035* (2013.01); *A61B 6/06* (2013.01); *A61B 6/42* (2013.01); *G21K 1/025* (2013.01); *H01J 35/02* (2013.01)

(58) Field of Classification Search
CPC .......... A61B 6/03; A61B 6/032; A61B 6/035; A61B 6/06; A61B 6/4035; G21K 1/02; G21K 1/025
See application file for complete search history.

(56) References Cited

U.S. PATENT DOCUMENTS 2,216,326 A * 10/1940 Smith ...................... G21K 1/10
378/158
4,277,685 A *  7/1981 Covic .................... G03B 42/02
378/150
(Continued)

FOREIGN PATENT DOCUMENTS

EP         2322096 A1    5/2011
WO    2012058207 A2    5/2012

*Primary Examiner* — Thomas R Artman
(74) *Attorney, Agent, or Firm* — Larry Liberchuck

(57) ABSTRACT

The invention relates to a system (100) for generating and collimating an X-ray beam (104), comprising an X-ray tube insert for generating the X-ray beam, the X-ray tube inert being a vacuum tube; a tube housing (102) for containing the X-ray tube insert (101), the tube housing being made of X-ray absorbing material; a collimator (103) for collimating the X-ray beam (104); wherein the collimator (103) is arranged in between the X-ray tube insert (101) and the tube housing (102). The invention also relates to a corresponding apparatus for scanning an object of interest with an X-ray beam (104) comprising the system.

10 Claims, 5 Drawing Sheets

(51) Int. Cl.
*A61B 6/03* (2006.01)
*A61B 6/00* (2006.01)
*H01J 35/02* (2006.01)

(56) References Cited

U.S. PATENT DOCUMENTS

| | | | |
|---|---|---|---|
| 4,672,648 A * | 6/1987 | Mattson | G21K 1/025 |
| | | | 378/149 |
| 5,384,820 A | 1/1995 | Burke | |
| 7,317,786 B2 * | 1/2008 | Distler | A61B 6/06 |
| | | | 378/145 |
| 7,852,990 B2 * | 12/2010 | Aulbach | G21K 1/04 |
| | | | 378/148 |
| 9,014,339 B2 * | 4/2015 | Grodzins | G01N 23/046 |
| | | | 359/233 |
| 9,020,103 B2 * | 4/2015 | Grodzins | G21K 1/046 |
| | | | 359/223.1 |
| 9,052,271 B2 * | 6/2015 | Grodzins | G01N 23/203 |
| 9,357,973 B2 * | 6/2016 | Mattson | G21K 1/10 |
| 9,424,958 B2 * | 8/2016 | Vogtmeier | G21K 1/10 |
| 10,056,164 B2 * | 8/2018 | Ofer | A61B 6/06 |
| 10,123,756 B2 * | 11/2018 | Karch | G21K 1/10 |
| 2002/0015474 A1 | 2/2002 | Tybinkowski | |
| 2002/0106056 A1 | 8/2002 | Mattson | |
| 2005/0243422 A1 * | 11/2005 | Distler | A61B 6/06 |
| | | | 359/566 |
| 2010/0074393 A1 * | 3/2010 | Thran | G21K 1/02 |
| | | | 378/4 |
| 2012/0106714 A1 | 5/2012 | Grodzins | |
| 2012/0269319 A1 * | 10/2012 | Grodzins | G01N 23/203 |
| | | | 378/51 |
| 2013/0294582 A1 | 11/2013 | Tsujii | |
| 2014/0112431 A1 * | 4/2014 | Mattson | G21K 1/10 |
| | | | 378/16 |
| 2014/0185739 A1 | 7/2014 | Tang | |
| 2015/0173692 A1 | 6/2015 | Heuscher | |
| 2015/0302946 A1 * | 10/2015 | Ofer | A61B 6/06 |
| | | | 378/160 |

\* cited by examiner

SYSTEM FOR GENERATING AND COLLIMATING AN X-RAY BEAM

CROSS-REFERENCE TO PRIOR APPLICATIONS

This application is the U.S. National Phase application under 35 U.S.C. § 371 of International Application No. PCT/EP2016/064381, filed on Jun. 22, 2016, which claims the benefit of International Patent Application No. PCT/CN2015/082704, filed on Jun. 29, 2015 and European Patent Application No. 15187275.1, filed on Sep. 29, 2015. These applications are hereby incorporated by reference herein.

FIELD OF THE INVENTION

The invention relates to an apparatus for scanning an object of interest with an X-ray beam, particularly to a system for generating and collimating an X-ray beam.

BACKGROUND OF THE INVENTION

X-ray imaging devices are used to obtain information about internal structures within an object of interest by irradiating the object with an X-ray beam generated by an X-ray source. For example, in medical X-ray imaging, those devices are used to obtain information about the inside structures (bones, organs . . . ) within a human body. An X-ray imaging device can acquire two-dimensional or three-dimensional images. For example, an X-ray imaging device can be a conventional X-ray imaging device for acquiring two-dimensional X-ray projection images, a C-arm X-ray imaging device, or a computer tomography (CT) device.

Conventionally, an X-ray source, often called X-ray tube, comprises a tube housing and an X-ray tube insert inside the tube housing. The X-ray tube insert is a vacuum tube, and comprises a so-called tube insert cap for sealing the tube. Inside the tube insert cap, there are a cathode for emitting electrons and an anode for emitting X-ray beam upon receiving the electrons. The tube housing protects the fragile vacuum tube. Typically, the tube housing is opaque to X-ray radiation and has an opening for allowing the X-ray beam to pass through. The emitted X-ray beam is directed towards a region of interest, for example a part of the patient's body. Since different tissues and/or bones within the patient's body have different levels of X-ray absorption, the X ray beam having passed through the region of interest is attenuated accordingly. The X ray beam having passed through the region of interest is then detected by an X-ray detector and the signal indicative of detected X-ray intensities, and the detected signal contains information about the internal structure within the patient's body and such information is retrieved, e.g. by forming X-ray images, accordingly.

A collimator can be used to collimate the X-ray beam generated by the X-ray source to be a slice of the X-ray beam passing through the region of interest. The collimator can be used to provide collimation for the X-ray beam so as to limit the size of the X-ray beam after passing through the collimator. For example, in typical CT systems, collimation is achieved by a blade set comprising of two moveable blades and a moveable plate with fixed slots or cams.

US2015/173692A1 discloses a device including a radiation source to emit radiation from a focal spot toward a volume of interest and a dynamic collimator located between the focal spot and the volume of interest.

WO2012/058207A2 discloses an X-ray beam scanner comprising a X-ray source and a collimator, which is stationary during image scanning, for collimating the X-ray beam so as to change the extent of the scan. The collimator is a standalone unit and is located outside the x-ray source, namely outside the tube housing which has an opening thereon. The inventor has recognized that such X-ray source and collimator as a whole are complex in structure.

OBJECT AND SUMMARY OF THE INVENTION

Therefore, it is advantageous to provide a system for generating and collimating an X-ray beam which mitigates and/or alleviates the above-mentioned problems.

According to a first aspect of the present invention, there is provided a system for generating and collimating an X-ray beam. The system comprises: an X-ray tube insert for generating said X-ray beam, said X-ray tube insert being a vacuum tube; a tube housing for containing said X-ray tube insert, said tube housing being made of an X-ray absorbing material; and a collimator for collimating said X-ray beam; wherein said collimator is arranged between said X-ray tube insert and said tube housing.

By having the collimator arranged in between the X-ray tube insert and the tube housing, it is not required to have additional space outside the tube housing. In this way, the system can be made much more compact in terms of weight and/or size. Consequently, the implementation in an apparatus of smaller size may be facilitated, and costs may be reduced.

In an embodiment of the system according to the present invention, the collimator comprises a plurality of collimating areas, and the collimator is adapted to be movable with respect to the tube insert so as to select one of the plurality of collimating areas for collimating the X-ray beam.

A selected one of the collimating areas is allowed to be moved in a position to collimate the X-ray beam. The multiple collimating areas enable multiple choices of collimation for the X-ray beam.

In another embodiment of the system according to the present invention, the plurality of collimating areas can be different in size and/or shape. Preferably, each of at least one collimating area is a slit.

The various size and/or shape of the slits forming the collimating areas allow multiple choices for collimation. As regards the size of the X-ray beam, multiple choices are possible after it has passed through a slit of a different size.

In an embodiment, each of at least one of the collimating areas is a completely material-free opening. In other words, the collimating area is a complete opening.

In another embodiment, each of at least one of the plurality of collimating areas comprises a plurality of pinholes.

In another embodiment, each of at least one collimating areas comprises a plurality of slots.

In another embodiment of the system according to the present invention, the collimator is adapted to rotate about an axis so as to select one of the collimating areas for collimating the X-ray beam, wherein the axis is perpendicular to an irradiation direction of the X-ray beam.

In an embodiment, said plurality of collimating areas is displaced at the same position along the axis perpendicular to an irradiation direction of the X-ray beam.

Rotating the collimator allows placing a given collimating area in front of the X-ray beam.

In another embodiment of the system according to the present invention, the collimator is adapted to translate along an axis so as to select one of the collimating areas for collimating the X-ray beam, wherein the axis is perpendicular to an irradiation direction of the X-ray beam.

For example, the axis can be a central axis of the X-ray tube insert.

In an embodiment, at least two of said plurality of collimating areas are displaced at different position along the axis perpendicular to an irradiation direction of the X-ray beam.

Translating the collimator allows placing one of the collimating areas to the propagating path of the X-ray beam.

In another embodiment of the system according to the present invention, the system further comprises an actuator for controlling the movement of the collimator.

The actuator allows the collimator to make rotating and/or translating movements along the central axis.

In another embodiment of the system according to the present invention, the collimator comprises a cylinder-shape portion and the plurality of collimating areas are arranged at a circumference surface of the cylinder-shaped portion of the collimator. For example, the collimating areas extends around the longitudinal axis of the cylinder-shaped collimator.

According to a second aspect of the present invention, an apparatus for scanning an object of interest with an X-ray beam is provided. The apparatus comprises: a system for generating and collimating the X-ray beam, and a detector for detecting the X-ray beam after the X-ray beam has passed through the object of interest.

Detailed explanations and other aspects of the invention will be given below.

BRIEF DESCRIPTION OF THE DRAWINGS

Particular aspects of the invention will now be explained with reference to the embodiments described hereinafter and considered in connection with the accompanying drawings, in which identical parts or sub-steps are designated in the same manner.

Each of FIG. 5A

DETAILED DESCRIPTION OF THE INVENTION

Figure 1:
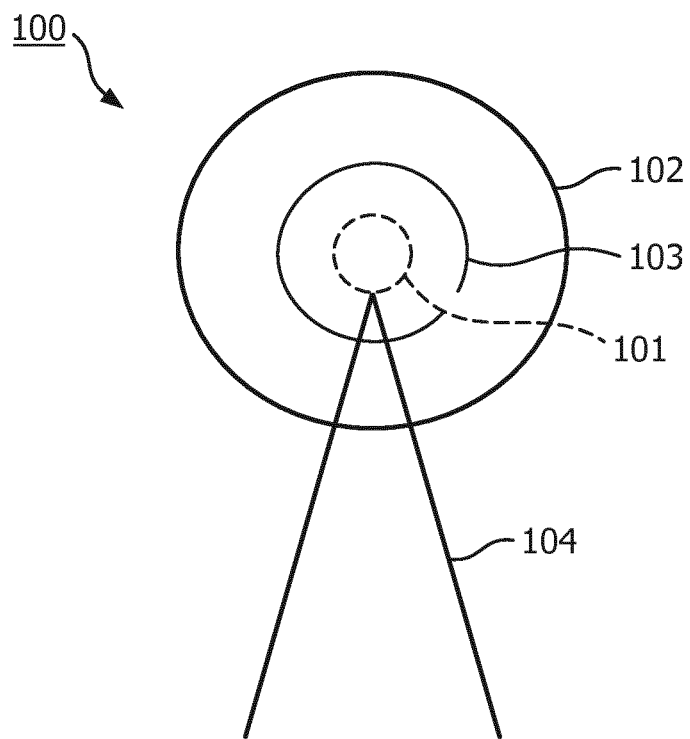
FIG. 1 depicts the longitudinal cross-sectional view of a system for generating and collimating an X-ray beam in accordance with an embodiment of the present invention;
Each of FIG. 2A

FIG. 1 depicts the longitudinal cross-sectional view of a system 100 for generating and collimating an X-ray beam in accordance with an embodiment of the present invention. The system 100 comprises an X-ray tube insert 101, a tube housing 102 for containing the X-ray tube insert 101, and a collimator 103. The X-ray tube insert 101 is a vacuum tube. A so-called tube insert cap is configured to seal the tube to provide the vacuum environment. Inside the tube insert cap, there are a cathode for emitting electrons and an anode for emitting X-ray beam upon receiving the electrons.

An X-ray beam 104 is generated by the X-ray tube insert 101. The tube housing 102 surrounds the X-ray tube insert 101. A collimator 103 is placed outside the X-ray tube insert 101 and inside the tube housing 102.

In an embodiment as illustrated in FIG. 1, the tube insert 101 comprises a cylinder-shaped portion, and the collimator 103 also comprises a cylinder-shaped portion and is arranged surrounding the cylinder-shaped portion of the tube insert 102.

The collimator 103 is mounted to either the outer surface of the X-ray tube insert 101, i.e. the outer surface of the tube insert cap, or the collimator 103 is mounted to the inner surface of the tube housing 102.

Figures 2A, 2B:
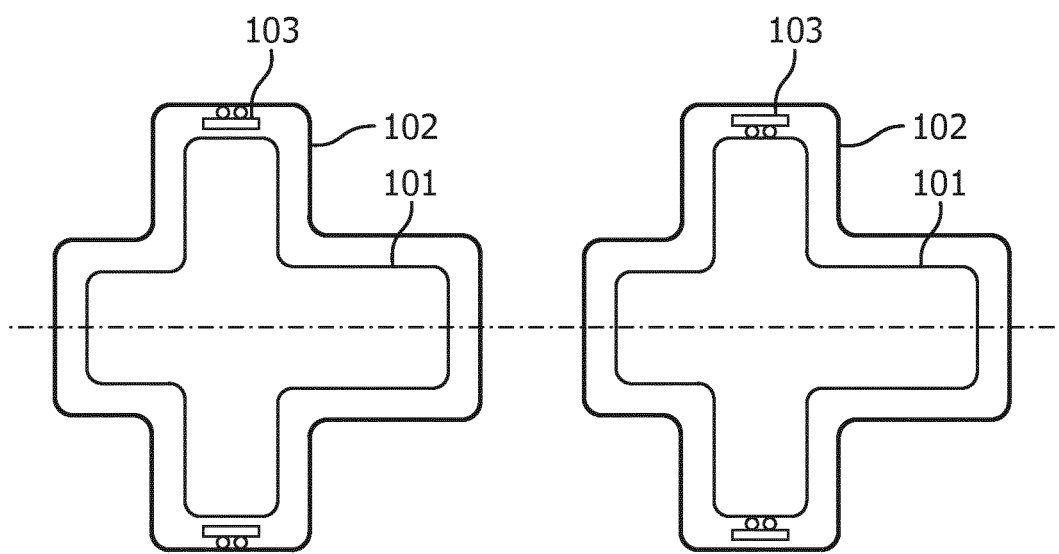
FIG. 2B depicts the transverse cross-sectional view of a system for generating and collimating an X-ray beam in accordance with an embodiment of the present invention so as to illustration the connections between the elements of the system.

For example, bearings are used to mount the collimator 103. The collimator 103 is mounted to one race of a bearing, and another race of the bearing is attached to either the outer surface of the X-ray tube insert 101 as illustrated in FIG. 2A or the inner surface of the tube housing 102 as illustrated in FIG. 2B. In another embodiment, the collimator 103 is made part of the race of the bearing. For example, the collimator 103 is the outer race of the bearing or inner race of the bearing.

The collimator 103 comprises at least one collimating area for collimating the X-ray beam. The X-ray beam 104 passes through the collimating area of the collimator 103 and then the tube housing 102, particularly an opening of the tube housing 102.

In some embodiments, the collimator 103 is made of X-ray absorbing material, for example, lead, tungsten, and an alloy thereof. Typically, the collimating area is an opening, such as a slit, of the collimator so as to allow the X-ray beam 104 to pass through.

Advantageously, the collimator 103 comprises a plurality of collimating areas 106, wherein the collimator 103 is adapted to be movable with respect to the tube insert so as to bring a selected one of the collimating areas into the X-ray beam for collimating the X-ray beam.

Figure 3:
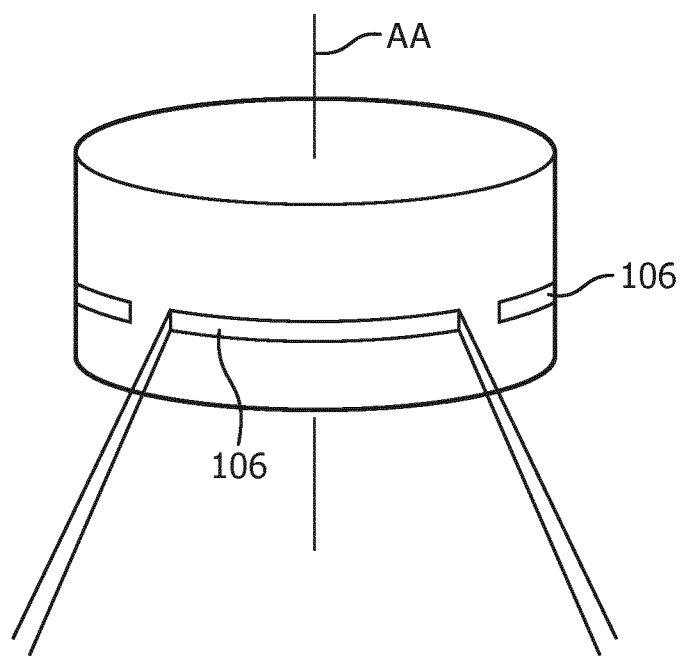
FIG. 3 depicts a three-dimensional view of an exemplary collimator in accordance with an embodiment of the present invention; Each of FIG. 4A, FIG. 4B

FIG. 3 depicts a three-dimensional view of a collimator in accordance with an embodiment of the present invention.

There are a plurality of collimating areas 106 on the collimator 103. During X-ray beam collimation, one of the plurality of collimating areas 106 is selected to be placed in the X-ray beam. The selected one of the plurality of collimating areas 106 is adapted to be moved to a specific position.

For example, if the X-ray beam is generated during CT (Computed Tomography) scanning, the size of the X-ray beam to be applied to the object of interest may be different. In order to cover the object of interest and avoid an unnecessary dose, a suitable size of the X-ray beam to be applied to the object of interest must be collimated. A plurality of collimating areas 106 allows multiple options for collimation. Meanwhile, selecting one of the plurality of collimating areas 106 is necessary for X-ray beam collimation for the specific object of interest.

Referring to the FIG. 3, the collimating area 106 can be a slit. Different collimating area 106 can be of different shape and/or size so as to collimate the X-ray beam into a different shape and/or size.

The collimating area, such as a slit, can be completely material-free, or comprises multiple openings. Each of FIG.

Figure 4A:
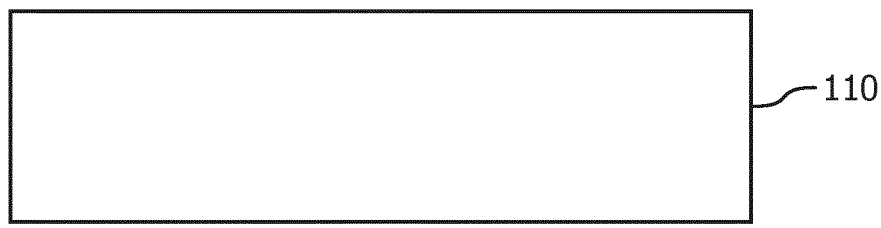
FIG. 4C depicts an exemplary collimating area of a collimator in accordance with an embodiment of the present invention.
Figure 4B:
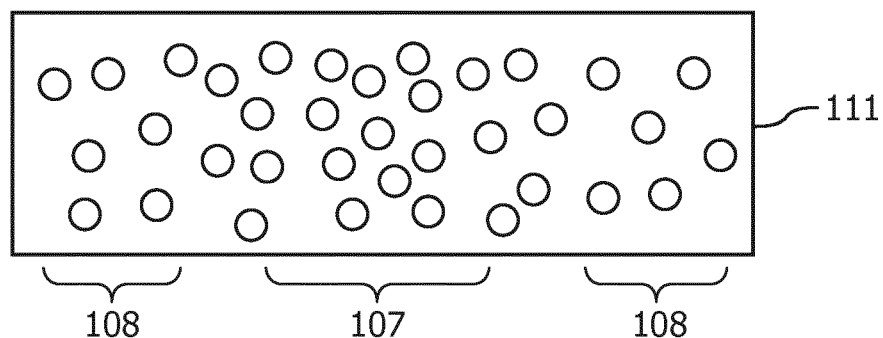
Figure 4C:
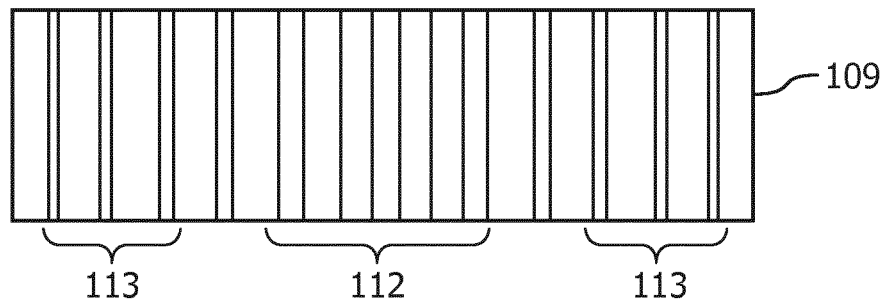

4A, FIG. 4B and FIG. 4C depict an exemplary collimating area in accordance with an embodiment of the present invention.

As illustrated in FIG. 4A, an example of the collimating area is a slit 110, which is completely material-free.

The collimator 103 comprises at least one collimating area. Accordingly, the collimator 103 comprises at least one open slit, each forming one collimating area.

Referring back to FIG. 3, in an embodiment, the collimator 103 is of a circular cylinder in shape, and each slit extends around the central axis AA, namely the longitudinal axis of the cylinder. The size of the at least one slit can be different from each other. In particular, the width of one slit, namely the dimension along the direction parallel to the central axis AA, and/or the length of the slit, namely the dimension the list extends, can be different.

With the slit 110, the X-ray radiation beam 104 is collimated to a fan-shaped beam. The width and the length of the slit 110 define the thickness and the fan angle of the collimated X-ray beam 104.

The thickness of the collimated X-ray beam 104 is dependent on the width of the slit 110. The wider the slit 110, the thicker the collimated X-ray beam 104 is. The fan angle of the collimated X-ray beam 104 is dependent on the length of the slit 110. The longer the length of the slit 110, the larger the fan angle is of the collimated X-ray beam 104.

The length of the slit 110 along the circumference of the collimator 103 depends on the diameter of the X-ray tube insert 101 and the number of slits. For example, the slit 110 has a length up to a few hundred millimetres for a CT scan.

The width of the slit 110 depends on a specific system design requirement. For example, the width of the slit 110 relates to a slice thickness for a CT scan. For example, the slit 110 has a width up to a few tens of millimetres.

In some embodiments, instead of being a complete opening, namely completely material-free, the collimating area can be "binary opening" be made of a series small slots or hols. Such "binary opening" is advantageous in reducing issues with scattered radiation which occur when the collimator is located very close to the focal point of the anode disk.

As illustrated in FIG. 4B, another example collimating area is not completely material-free, but comprises a plurality of pinholes 111.

For example, the lateral dimensions of a given collimating area range between a few centimetres and a few tens of centimetres. For example, the number of pinholes 111 is more than 100, preferably more than 1000. The pinholes may be provided in a regular pattern or irregularly, for example randomly distributed.

As illustrated in FIG. 4C, another example collimating area is not completely material-free, but comprises a plurality of slots 109 extending along the width direction of the collimating area.

Referring back to FIG. 3, the collimator 103 is adapted to rotate about the axis AA, and the collimator 103 is so mounted to the X-ray tube insert that the X-ray beam is irradiated along a direction perpendicular to the central axis AA. In an embodiment, the axis AA is the central axis AA of the X-ray tube insert 101.

Further, the collimator 103 comprises a plurality of collimating areas 106, each extending around the central axis AA and being adjacent to each other. By rotating the collimator 103, one collimating area of the plurality of collimating areas 106 is moved so as to be in the X-ray beam 104 and thus be selected to collimate the X-ray beam 104.

The rotation of the collimator 103 enables any one of the plurality of collimating areas 106 to be moved into the X-ray beam 104. During the rotation, the step of the rotation angle of the collimator 103 is defined by an angular position difference of the plurality of collimating areas 106. For example, for a collimator with five slits, the angular position difference is 72 degrees (360/5=72), hence the step of the rotation angle is 72 degrees.

Alternatively or additionally, the collimator 103 is adapted to translate along the axis AA.

By translating the collimator 103 along a central axis AA, one collimating area of the plurality of collimating areas 106 is moved to be in the X-ray beam 104.

For example, the translation of the collimator 103 is enabled by thread transmission. The thread is on the collimator 103 and the X-ray tube insert 101, or the thread is on the collimator 103 and the tube housing 102.

The translation range of the collimator 103 relates to the available space inside the tube housing 102. The total required width of the plurality of collimating areas 106 and the conjunction material length in between together defines the total translation distance of the collimator 103.

Figure 5A:
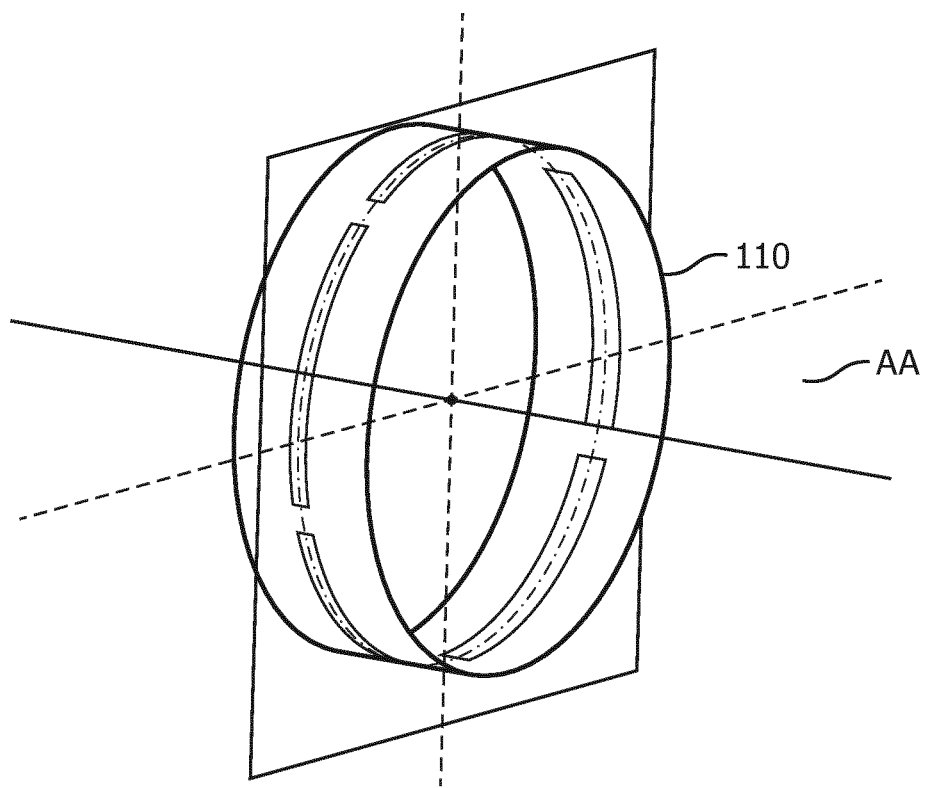
FIG. 5B depicts an exemplary collimator in accordance with an embodiment of the present invention.
Figure 5B:
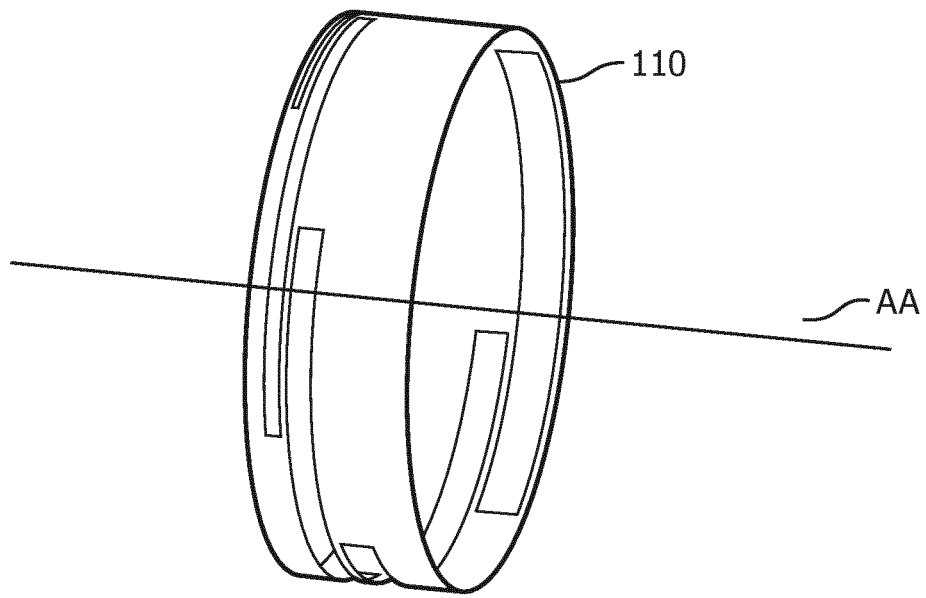

Each of FIG. 5A and FIG. 5B depicts an exemplary collimator in accordance with an embodiment of the present invention.

In an embodiment as illustrated in FIG. 5A, the collimator is cylinder in shape and has a central axis AA. A plurality of collimating areas, such as a plurality of slits 110 are located at the same position along the central axis AA. For example, the slits 110 comprise a symmetry axis in a same plane perpendicular to the central axis AA. Various slits which comprising a symmetry axis in a same plane perpendicular to the central axis allow placing one of the selected slits in front of the X-ray radiation beam, by rotating the collimator.

The direction of the symmetry axis of the slits 110 is along the circumference of the collimator 103.

FIG. 5A illustrates an example of the slits 110 in accordance with this embodiment. For example, the number of slits 110 can be five.

More generally, the number of collimating areas 106 depends on the range of the X-ray beam collimation system. For example, for a low-end X-ray beam collimation system, two collimating areas may be used to provide two options for collimation.

However, to meet most systems requirements, a number of five collimating areas is a good compromise between flexibility and practical use.

The larger the number of collimating areas, the more collimation options there are to choose from. On the other hand, the larger the number of collimating areas, the smaller the size of the collimating areas is, which means the smaller the size of the X-ray beam after passing through the collimator 103.

For example, a CT collimation requires a fan beam angle to be 50~60 degrees in front view. With five collimating areas regularly spaced over a circular ring, the fan beam angle is around 72 degrees if the symmetry axis of all five slits is a same plane perpendicular to the central axis AA.

In another embodiment as illustrated in FIG. 5B, the plurality of collimating areas, such as the plurality of slits 110 extending around the axis AA and displaced at a different position along the axis AA. For example, the slits 110 comprise a symmetry axis at different parallel planes perpendicular to the axis AA. Various slits comprising a symmetry axis in different parallel planes perpendicular to the central axis allow placing one of the selected slits in front of the X-ray beam by rotating and translating the collimator.

FIG. 5B illustrates an example of the slits 110 in accordance with this embodiment.

In a preferable embodiment of the system, the movement of the collimator 103 comprises both rotation around the axis AA and translation along the axis AA at the same time. In a practical embodiment, the length along the circumference of a slit of the slits 110 may be at least equal to a half-length of the circumference of the collimator 103. Therefore, the length along the circumference of a slit of the slits 110 is long enough to cover the specific collimating area when rotated to the specific collimating area.

In some embodiments, the pinholes 111 have a density at a center region 107 of the at least one of the collimating areas which is higher than at border regions 108 of the at least one of the collimating areas.

The density of the pinholes is higher at a center region 107 than at border regions 108, such that the transparency to the X-ray beam 104 is higher at the center region 107 than at border regions 108. Therefore, the intensity of the X-ray beam 104 after passing through the pinholes is higher at the center region 107 than at border regions 108.

For example, in a CT scan, the X-ray beam is emitted towards a part of a human body. The human body is thicker at a center region of the human body than at border regions of the human body. Therefore, the necessary X-ray beam intensity is more important at the center region of the human body than at the border regions of the human body.

In some embodiments, in at least one of the collimating areas, the slots 109 are arranged parallel to each other along a direction transverse with respect to the axial direction of the at least one of the collimating areas, and are separated from each other by a plurality of X-ray absorbing regions, the width of the slots 111 at a center region 112 of the at least one of the collimating areas being larger than at border regions 113 of the at least one of the collimating areas.

The width of the slots is larger at a center region 112 than at border regions 113, such that the transparency to the X-ray beam 104 is higher at the center region 112 than at border regions 113. Therefore, the intensity of the X-ray beam 104 after passing through the slots is higher at the center region 112 than at border regions 113.

In some embodiments, in the system 100, the collimator 103 is cylinder-shaped.

As illustrated in FIG. 3, the collimator 103 is cylinder-shaped, or in other words, of a cylindrical shape, which is the same shape as a portion of the X-ray tube insert 101 and/or the tube housing 102 where it is mounted.

In some embodiments, the system 100 may further comprise an actuator 301 (not shown) for controlling the movement of the collimator 103.

The actuator 301 is connected to the collimator 103. The movement of the collimator 103, including rotation along the central axis and translation along the central axis, is controlled by the actuator 301.

For example, the actuator 301 corresponds to a step motor or a servo motor.

Figure 6:
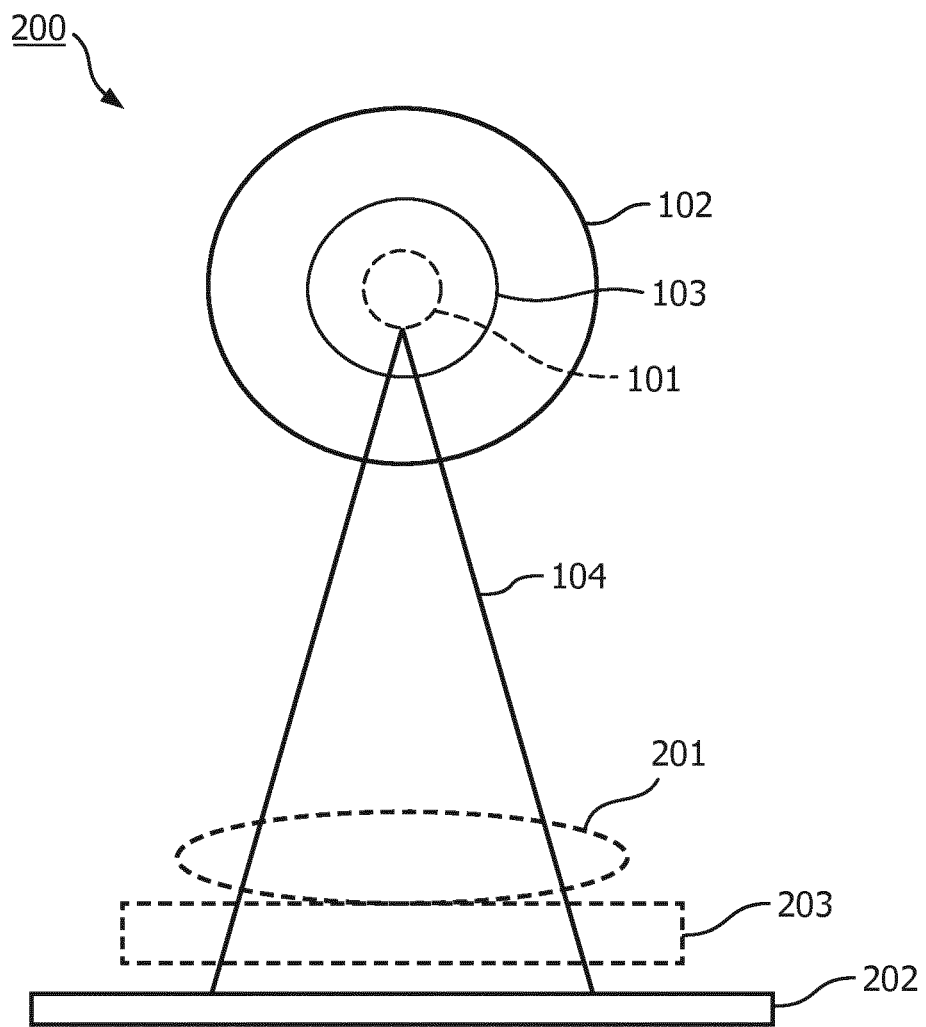
FIG. 6 depicts a schematic design of an apparatus for scanning an object of interest with an X-ray in accordance with an embodiment of the present invention.

FIG. 6 depicts a schematic design of an apparatus 200 for scanning an object of interest 201 with an X-ray beam 104 in accordance with an embodiment of the present invention.

The apparatus 200 comprises a system for generating and collimating an X-ray beam 104, and a detector 202 for detecting the X-ray beam 104 after the X-ray beam has passed through the object of interest 201. The apparatus 200 can further comprise a processor for generating an image on basis of a signal indicative of the intensity of the X-ray beam 104 detected by the detector 202.

A support 203 is used for supporting the object of interest 201. The support 203 is placed between the system 100 and the detector 202. A console (not shown) connects to the detector 202. The console can process the signal received from the detector 202 and visualize the signal on a display.

The detector 202 detects the X-ray radiation beam after the beam has passed through the object of interest 201 and the support 203, and generates an image accordingly. The generated image is sent to the console and visualized on a display subsequently.

The above embodiments as described are only illustrative, and not intended to limit the technique approaches of the present invention. Although the present invention is described in details referring to the preferable embodiments, those skilled in the art will understand that the technique approaches of the present invention can be modified or equally displaced without departing from the scope of the technique approaches of the present invention, which will also fall into the protective scope of the claims of the present invention. In the claims, the word "comprising" does not exclude other elements or steps, and the indefinite article "a" or "an" does not exclude a plurality. Any reference signs in the claims should not be construed as limiting the scope.

The invention claimed is:

1. A system for generating and collimating an X-ray beam, comprising:
   an X-ray tube insert for generating said X-ray beam;
   a tube housing for containing said X-ray tube insert, said tube housing being made of an X-ray absorbing material; and
   a collimator for collimating said X-ray beam;
   wherein said collimator is arranged between said X-ray tube insert and said tube housing, wherein said collimator comprises a plurality of collimating areas, and wherein said collimator is adapted to be movable with respect to the X-ray tube insert so as to select one of the plurality of collimating areas for collimating the X-ray beam;
   wherein at least one collimating area of the plurality of collimating areas comprises a plurality of binary openings, said binary openings having a higher density in a center region of a collimating area than at border regions of the collimating area.

2. The system as claimed in claim 1, wherein a binary opening of the plurality of binary openings is at least one of a pinhole and a slot.

3. The system as claimed in claim 1, wherein said collimator is adapted to rotate around an axis so as to select one of the collimating areas for collimating the X-ray beam, the axis being perpendicular to an irradiation direction of the X-ray beam.

4. The system as claimed in claim 3, wherein said plurality of said collimating areas are displaced at the same position along the axis.

5. The system as claimed in claim 1, wherein said collimator is adapted to translate along an axis of said X-ray tube insert so as to select one of the collimating areas for collimating the X-ray beam, the axis being perpendicular to an irradiation direction of the X-ray beam.

6. The system as claimed in claim 5, wherein at least two collimating areas of said plurality of collimating areas are displaced at a different position along the axis.

7. The system as claimed in claim 1, wherein the tube insert comprises a cylinder-shaped portion, and the collimator comprises a cylinder-shaped portion and is arranged to surround the cylinder-shaped portion of the tube insert.

8. The system as claimed in claim 1, wherein said collimator comprises a cylinder-shaped portion, and the plurality of collimating areas are arranged at a circumference surface of the cylinder-shaped portion of the collimator.

9. The system as claimed in claim 1, further comprising:
an actuator configured to move said collimator.

10. An apparatus for scanning an object of interest with an X-ray beam, said apparatus comprising:
a system for generating and collimating the X-ray beam as claimed in claim 1; and
a detector for detecting said X-ray beam after said X-ray beam has passed through the object of interest.

* * * * *